(12) United States Patent
De Man et al.

(10) Patent No.: US 7,388,940 B1
(45) Date of Patent: Jun. 17, 2008

(54) ARCHITECTURES FOR CARDIAC CT BASED ON AREA X-RAY SOURCES

(75) Inventors: Bruno K. B. De Man, Clifton Park, NY (US); Norbert J. Pelc, Los Altos, CA (US)

(73) Assignees: General Electric Company, Schenectady, NY (US); The Board of Trustees of The Leland Stanford Junior University, Stanford, CA (US)

( * ) Notice: Subject to any disclaimer, the term of this patent is extended or adjusted under 35 U.S.C. 154(b) by 0 days.

(21) Appl. No.: 11/563,065

(22) Filed: Nov. 24, 2006

(51) Int. Cl.
*G01N 23/083* (2006.01)
(52) U.S. Cl. .............................. 378/9; 378/4
(58) Field of Classification Search ............ 378/4, 378/9, 15, 19, 8, 197, 198
See application file for complete search history.

(56) References Cited

U.S. PATENT DOCUMENTS

| | | | |
|---|---|---|---|
| 4,196,352 A | 4/1980 | Berninger et al. | |
| 4,384,359 A | 5/1983 | Franke | |
| 4,991,190 A | 2/1991 | Mori | |
| 5,848,117 A | 12/1998 | Urchuk et al. | |
| 5,966,422 A | 10/1999 | Dafni et al. | |
| 6,324,258 B1 * | 11/2001 | Beekman | 378/145 |
| 6,421,412 B1 | 7/2002 | Hsieh et al. | |
| 6,483,892 B1 | 11/2002 | Wang et al. | |
| 6,876,719 B2 | 4/2005 | Ozaki | |
| 6,947,522 B2 | 9/2005 | Wilson et al. | |
| 6,983,035 B2 | 1/2006 | Price et al. | |
| 7,039,153 B2 | 5/2006 | Bruder et al. | |
| 7,062,006 B1 | 6/2006 | Pelc et al. | |
| 2003/0043957 A1 | 3/2003 | Pelc | |
| 2004/0114710 A1 | 6/2004 | Ozaki | |
| 2004/0213371 A1 | 10/2004 | Bruder et al. | |
| 2005/0190878 A1 | 9/2005 | De Man et al. | |
| 2006/0002506 A1 | 1/2006 | Pelc | |
| 2006/0133563 A1 * | 6/2006 | Hopkins et al. | 378/5 |
| 2006/0210015 A1 * | 9/2006 | Pelc et al. | 378/9 |

* cited by examiner

*Primary Examiner*—Hoon Song
(74) *Attorney, Agent, or Firm*—Ziolkowski Patent Solutions Group, SC

(57) ABSTRACT

A CT imaging system includes a rotatable gantry having an opening to receive an object to be scanned having a small field-of-view (FOV) inside a large FOV. A plurality of area sources is attached to the rotatable gantry, each area source includes a plurality of x-ray emission sources, wherein the plurality of area sources are configured to emit x-rays toward the object. A plurality of x-ray detector arrays is attached to the gantry and positioned such that at least a first detector array and a second detector array each receive x-rays that pass through at least the entire small FOV of the object.

20 Claims, 6 Drawing Sheets

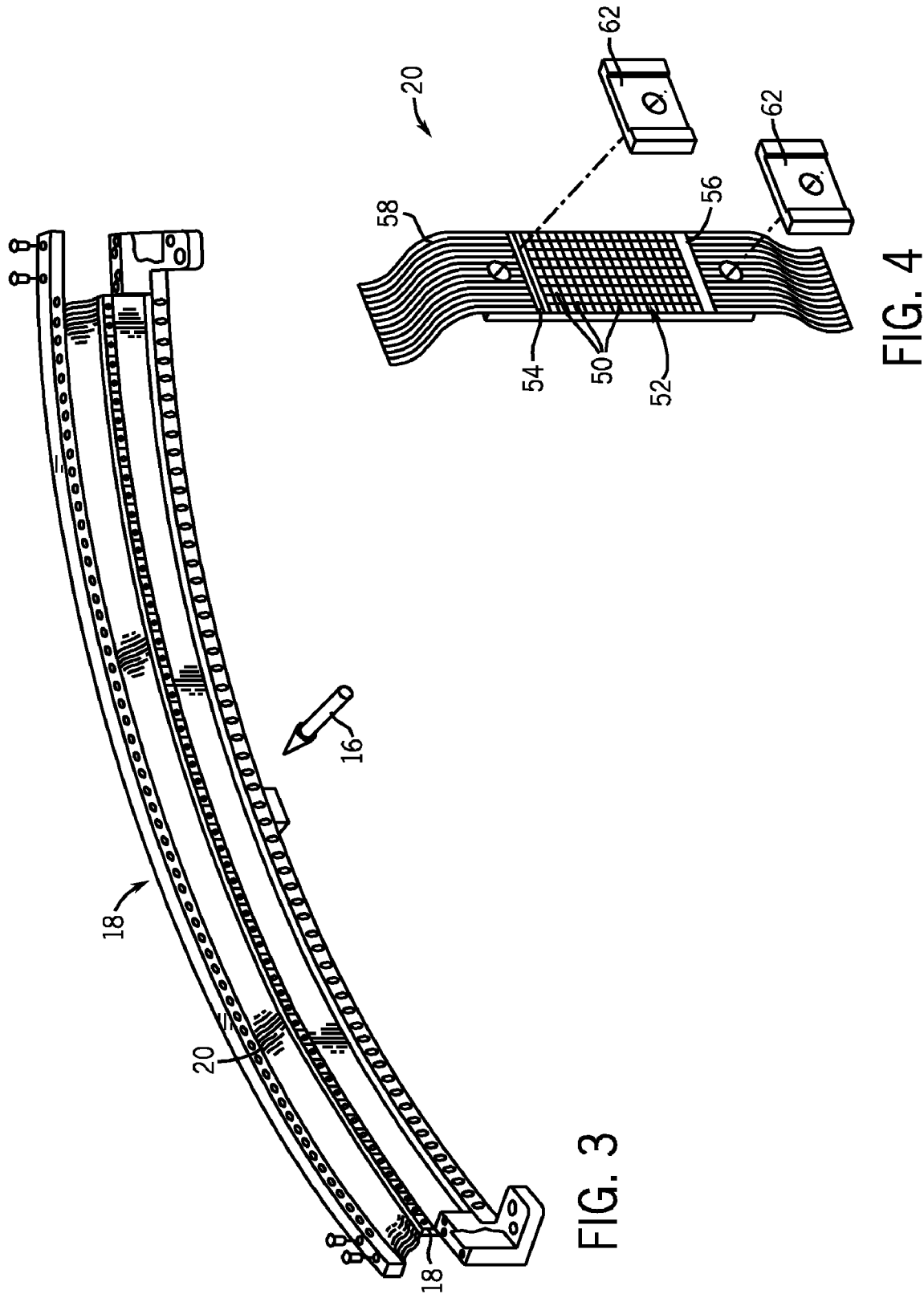

ARCHITECTURES FOR CARDIAC CT BASED ON AREA X-RAY SOURCES

BACKGROUND OF THE INVENTION

The present invention relates generally to diagnostic imaging and, more particularly, to a method and apparatus of cardiac CT imaging using multi-spot emission sources.

Typically, in computed tomography (CT) imaging systems, an x-ray source emits a cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a scintillator for converting x-rays to light energy adjacent the collimator, and photodiodes for receiving the light energy from the adjacent scintillator and producing electrical signals therefrom, although other types of detectors, including direct-conversion detectors, are known.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

It is generally desirable to have increased speed, coverage, and resolution of CT scanners, for example to improve imaging of the cardiac region. In recent years, manufacturers have improved scanners by increasing the gantry speed, by reducing the pixel size, and by extending the coverage of the detectors in the Z direction by extending the length of the detector in the Z direction. This approach has resulted in development of CT systems that have larger detectors. Detectors, in principle, may be extended in the Z direction to cover the entire cardiac region. However, such a length may be undesirable for a number of reasons. For instance, large detectors add cost and complexity to a CT system, not only in the detector components themselves, but in the data acquisition systems required to read out the increased number of channels. The increased detector size also results in an increased mass of the detector, thereby resulting in increased mechanical stresses in the components of the CT system.

As detectors get longer in the axial (Z) direction, an increase in the cone angle occurs as well. The cone angle is the angle, along the Z direction, between the focal spot and the edges of the detector. The increase in cone beam angle leads to cone beam artifacts in reconstructed images. Beyond a certain limit, the cone beam becomes severe, and increased scan coverage may not be accomplished by simply increasing the length of the detector along the Z direction.

A complete dataset is typically acquired during a rotation of a CT gantry through approximately 180 degrees, thereby defining the temporal resolution of a CT scanner, ignoring cone angles. Accordingly, the temporal resolution may be improved by spinning the gantry faster. However, mechanical stresses therein substantially increase with increased gantry speed, thereby imposing practical limits on the upper speed of the gantry.

Therefore, it would be desirable to design a CT apparatus and method to improve image quality of the cardiac region while increasing Z coverage of a subject.

BRIEF DESCRIPTION OF THE INVENTION

The present invention is a method and apparatus for improving temporal resolution of cardiac imaging by use of a CT system, and reducing conebeam artifacts in a CT system by employment of inverse geometry CT configurations of detectors and emission sources.

According to one aspect of the present invention, a CT imaging system includes a rotatable gantry having an opening to receive an object to be scanned having a small field-of-view (FOV) inside a large FOV. A plurality of area sources is attached to the rotatable gantry, each area source includes a plurality of x-ray emission sources, wherein the plurality of area sources are configured to emit x-rays toward the object. A plurality of x-ray detector arrays is attached to the gantry and positioned such that at least a first detector array and a second detector array each receive x-rays that pass through at least the entire small FOV of the object.

According to another aspect of the present invention, a method of fabricating a CT imaging system includes attaching a pair of multiple-emitter x-ray area sources to a rotatable gantry and attaching a plurality of detector arrays to the rotatable gantry. The method includes positioning a first detector array of the plurality of detector arrays such that x-rays emanating from a first x-ray area source of the pair of multiple-emitter x-ray area sources pass through an entire cardiac region of a subject are impinged thereon. The method further includes positioning a second detector array of the plurality of detector arrays such that x-rays emanating from a second x-ray area source of the pair of multiple-emitter x-ray area sources and passing through the entire cardiac region of a subject are impinged thereon.

According to yet another aspect of the present invention, an imaging system includes a first area source having a plurality of point emission x-ray sources configured to emit x-rays toward a patient. The system includes a first detector array configured to receive x-rays emitted from the first area source that pass through at least a cardiac region of the patient, a second area source comprising a plurality of point emission x-ray sources configured to emit x-rays toward the patient, and a second detector array configured to receive x-rays emitted from the second area source that pass through at least the cardiac region of the patient.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

DETAILED DESCRIPTION OF THE PREFERRED EMBODIMENT

The operating environment of the present invention is described with respect to a sixteen-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
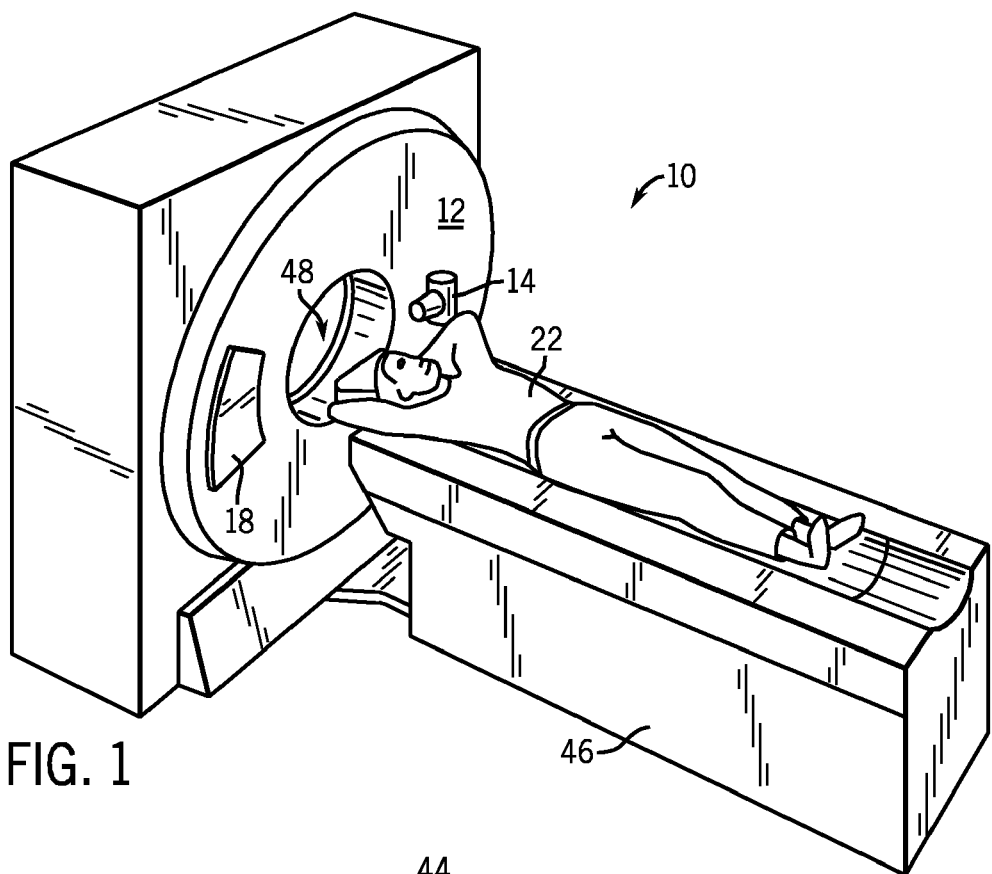
FIG. 1 is a pictorial view of a CT imaging system.
Figure 2:
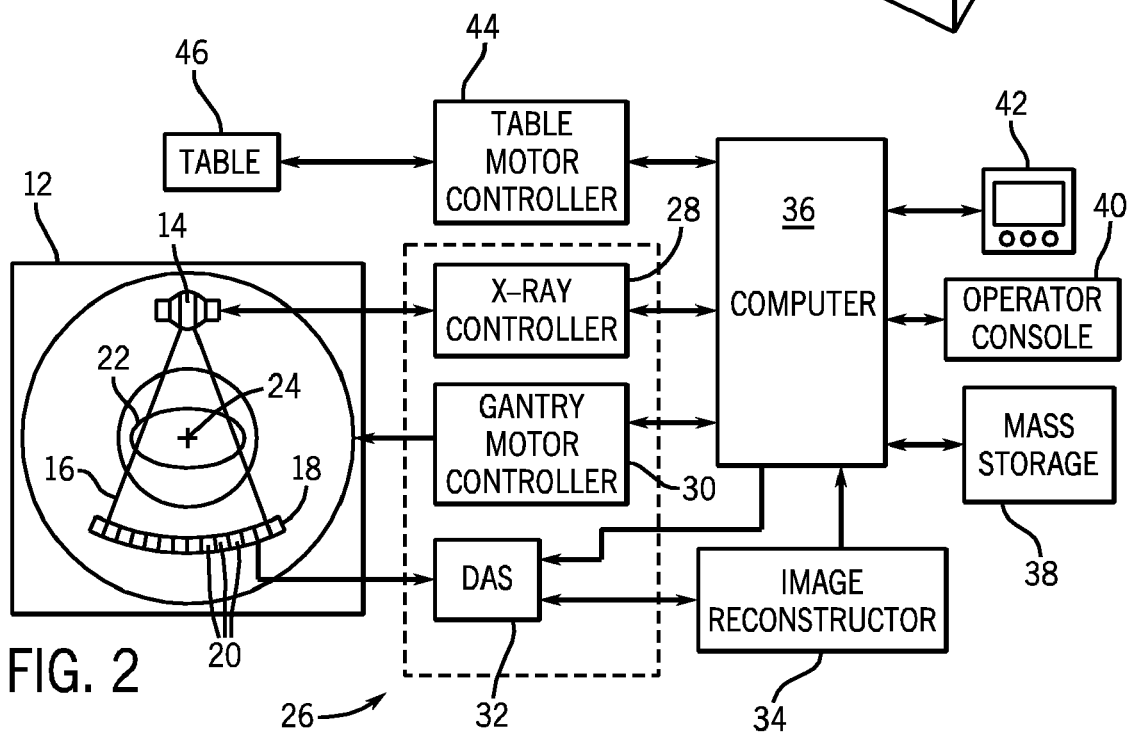
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) may be positioned above scintillator array 56 to collimate x-ray beams 16 in one or both directions before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

According to an embodiment of the present invention, the temporal resolution of the CT system 10 is improved by increasing the angular coverage of the system by adding detector arrays having multiple detectors and x-ray emission area source arrays having multiple x-ray emission sources about the gantry as described below in FIGS. 5-7. In this manner, the detectors may be illuminated by the x-ray emission area source arrays that are positioned in the gantry such that a subject to be scanned is between the detectors and a corresponding x-ray emission area source array. Accordingly, the detectors may receive data which pass through a cardiac field-of-view of the subject, a non-cardiac field-of-view of the subject, or both. In one embodiment, x-ray emission sources may include, but are not limited to, solid state x-ray sources, thermionic x-ray sources, field emitters, and the like. To reduce conebeam effects, the x-ray emission area source arrays illustrated in FIGS. 5-7 may also extend in a Z direction of the CT system.

Figure 5:
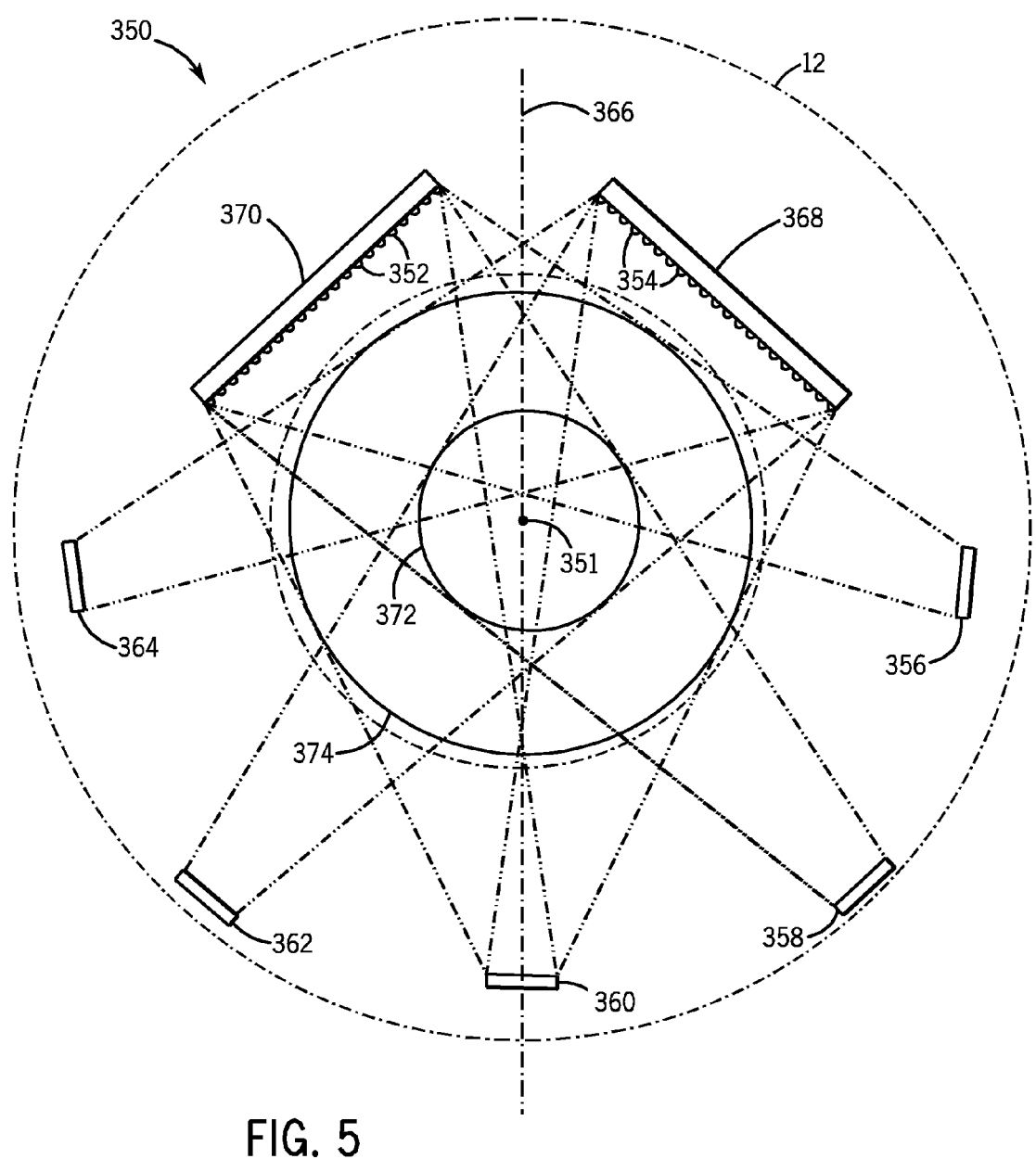
FIG. 5 is a schematic diagram of an arrangement of a plurality of emission sources and a plurality of detector arrays of a CT system according to another embodiment of the present invention.

FIG. 5 is an axial view of the gantry 12 of the CT system 10 of FIG. 1 according to another embodiment. Gantry 12 includes a plurality of emission sources 352, 354 positioned on area source arrays 370 and 368, respectively. Area source arrays 368, 370 are attached to the gantry 12 and symmetrically positioned with respect to a line of symmetry 366 passing transversely through a center 351 of the gantry 12. Gantry 12 also includes an array of detector arrays 356-364 attached thereto, which may be symmetrically positioned with respect to line of symmetry 366. Area source arrays 368, 370, and detector arrays 356-364 may, in the alternative, be positioned asymmetrically as well. Detector arrays 362 and 364 are impinged upon by x-rays emitting from source array 368, and detector arrays 356 and 358 are impinged upon by x-rays emitting from source array 370. Detector array 360 receives x-rays emitting from both source arrays 368 and 370. Accordingly, a cardiac region, or small FOV, 372 is fully imaged by both detector arrays 358 and 362, and a peripheral region outside the small FOV but within a large FOV 374 is imaged by detector arrays 356, 360, and 364, which additionally provide overlapping information with small FOV 372, thereby providing improved temporal resolution of the cardiac region 372. Detector arrays 356 and 364 are illustrated as receiving x-rays emitting from their respective source arrays, 370 and 368. However, one skilled in the art will recognize that detector arrays 356 and 364 may be positioned to receive x-rays that only pass through a peripheral region within the large FOV 374, but outside the small FOV 372.

Figure 6:
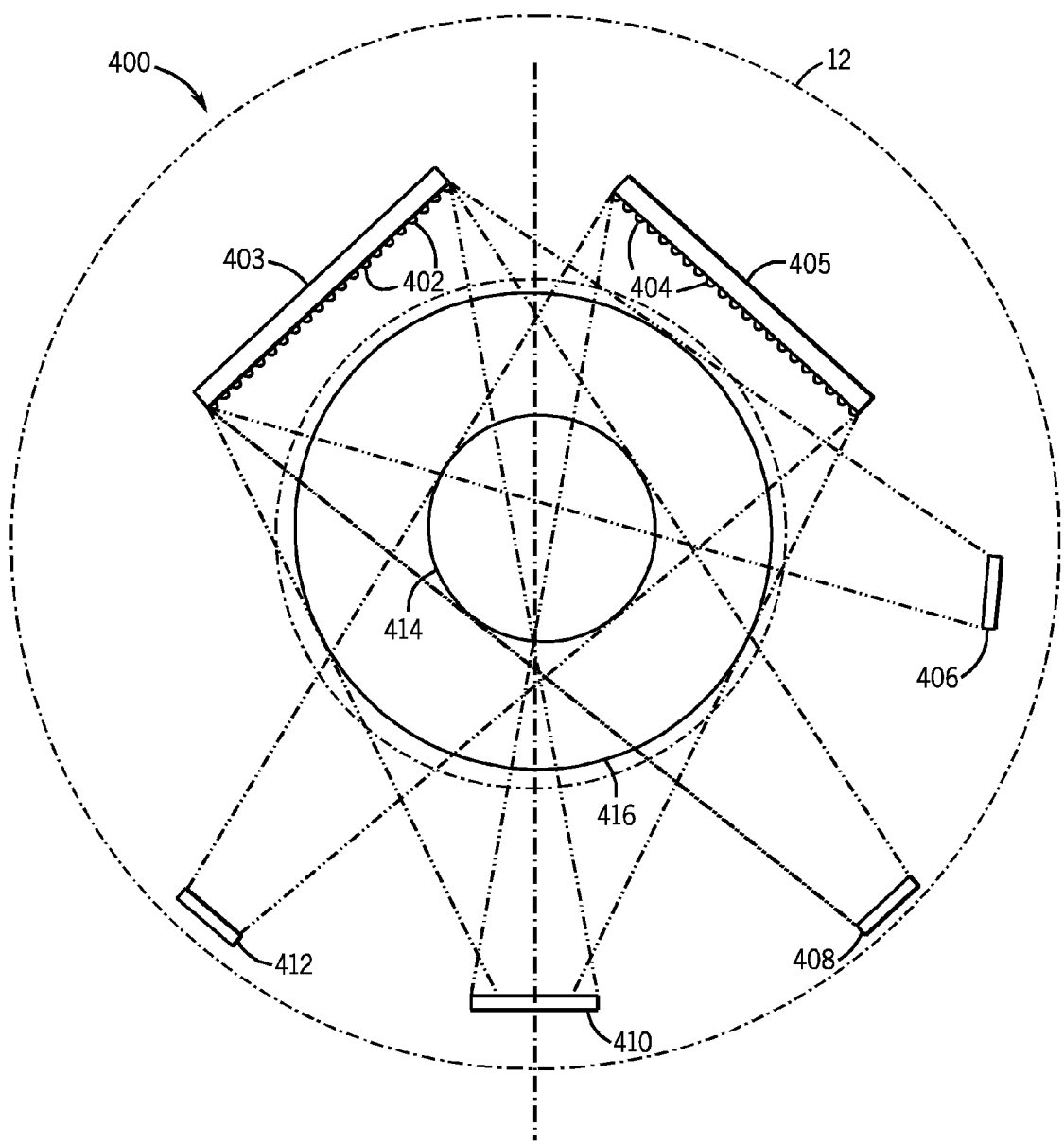
FIG. 6 is a schematic diagram of an arrangement of a plurality of emission sources and a plurality of detector arrays of a CT system according to another embodiment of the present invention.

FIG. 6 is an axial view of the gantry 12 of the CT system 10 of FIG. 1 according to another embodiment. Gantry 12 includes a pair of emission source arrays 403, 405, which may be arranged symmetrically about line of symmetry 401, or may be aligned asymmetrically. Each emission source array 403, 405 has a plurality of emission sources 402, 404 positioned, respectively, thereon. Gantry 12 also includes a plurality of detector arrays 406, 408, 410, and 412 that are asymmetrically positioned with respect to source arrays 402, 404. Detector arrays 406, 408, and 410 are impinged upon by x-rays emitting from emission source array 403, and detector array 412 is impinged upon by x-rays emitting from emission source array 405. Accordingly, a cardiac region, or small FOV 414 may be fully imaged by both detector arrays 408 and 412, and a large FOV 416, is imaged by all detector arrays 406 and 410, thereby providing improved temporal resolution of the cardiac region.

In an alternative embodiment, still referring to FIG. 6, source array 403 may be extended in length (not illustrated) such that x-rays emitting therefrom, and passing through the entire large FOV 416, impinge upon detector array 408, providing full coverage thereof. In conjunction, detector array 405 may be caused to emit x-rays that pass through small FOV 414 as illustrated. Accordingly, the operation of the combination in this embodiment provides improved temporal resolution of the cardiac region, or small FOV 414 by such operation.

In yet another alternative embodiment, detector arrays 403 and 405 may be extended in length (not illustrated) such that x-rays emitting therefrom provide additional small FOV 414 and large FOV 416 coverage. As such, extended emission array 403 may be positioned such that x-rays emitting therefrom pass through the entire small FOV 414 and an entire peripheral region outside the small FOV 414, to a tangential edge of large FOV 414. Likewise, extended emission array 405 may be positioned such that x-rays emitting therefrom pass through the entire small FOV 414 and an entire peripheral region outside the small FOV 414, to a tangential edge of large FOV 414. Such operation may be performed without operation of detector arrays 406 and 410. Accordingly, the operation of the combination in this embodiment provides improved temporal resolution of the cardiac region, or small FOV 414 by such operation.

Figure 7:
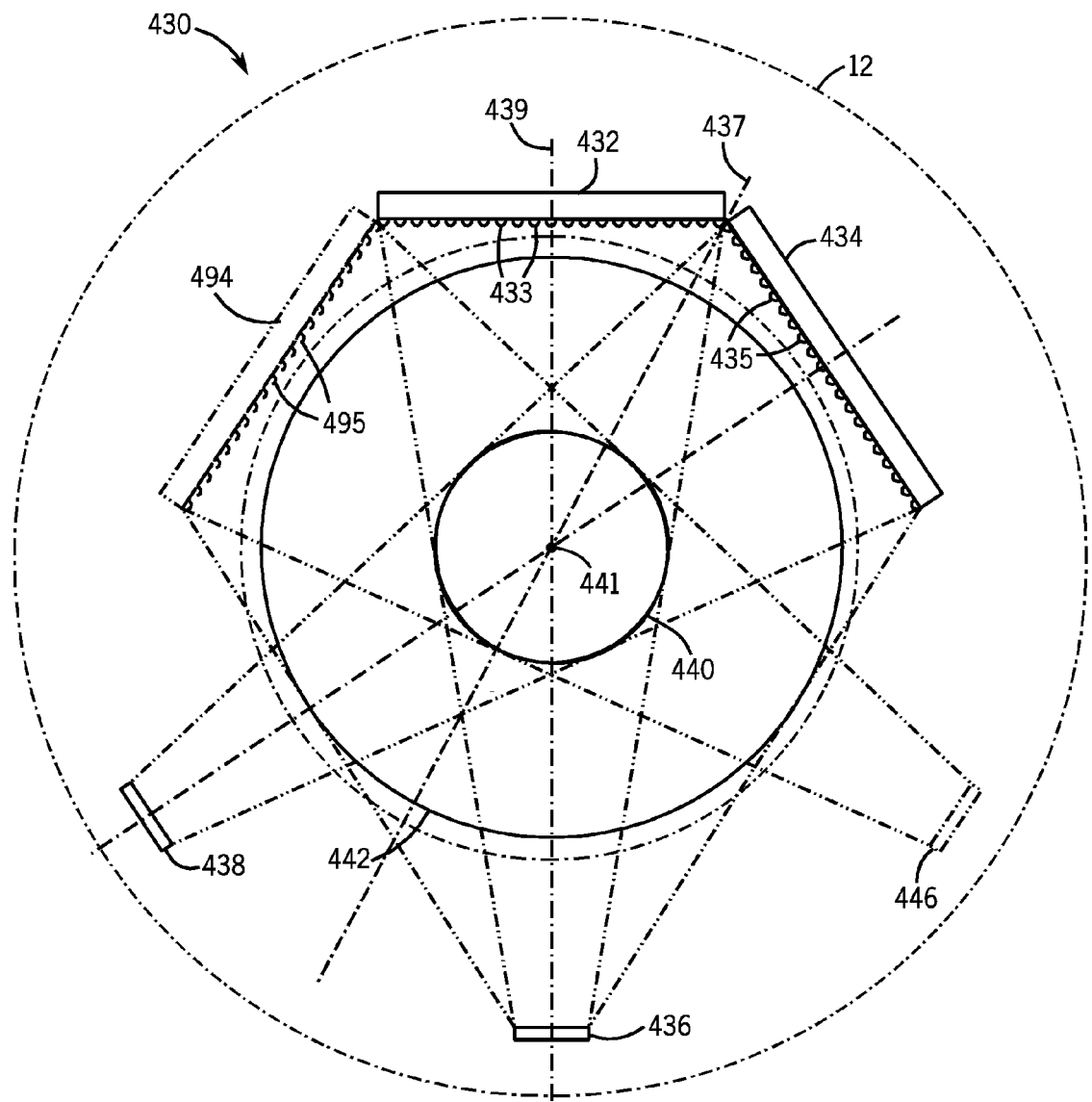
FIG. 7 is a schematic diagram of an arrangement of a plurality of emission sources and a plurality of detector arrays of a CT system according to another embodiment of the present invention.

FIG. 7 is an axial view of the gantry 12 of the CT system 10 of FIG. 1 according to another embodiment. Gantry 12 includes a first emission source array 432 and a second emission source array 434, each having a plurality of emission sources 433, 435 positioned respectively, thereon, about first line of symmetry 437. Gantry 12 includes a plurality of detector arrays 436, 438 that may be symmetrically positioned with respect to arrays 432, 434 and with respect to first line of symmetry 437. Detector array 436 is impinged upon by x-rays emitting from emission array 432, and detector array 438 is impinged upon by x-rays emitting from emission array 434. Accordingly, a cardiac region, or small FOV 440, and a large FOV 442 is fully imaged by detector arrays 436, 438, thereby providing improved temporal resolution of the cardiac region.

In another embodiment, detector arrays 436, 438 are configured to be additionally impinged upon by x-rays emitting from emission arrays 434 and 432 to provide additional coverage of large FOV 442.

In still another embodiment, a third emission source array 494 having a plurality of emission sources 495 is attached to the gantry 12. Detector array 446 is positioned opposite a cardiac region, or small FOV, 440 to receive x-rays that pass therethrough, thereby providing additional imaging information of the cardiac region 440 and improved temporal resolution thereof in addition to the imaging information provided by detector arrays 436, 438. Emission source arrays 433, 435, 494 and detector arrays 436, 438, 446 may be symmetrically positioned with respect to a second line of symmetry 439 passing transversely through a center 441 of the gantry 12.

Referring still to FIG. 7, one skilled in the art will recognize that additional combinations of x-ray impingement may exist between area source arrays 432, 434, and 444 with respect to the detector arrays 436, 438, and 442 illuminated. For instance, in yet another embodiment, emission source array 432 may be operated in conjunction with detector array 436 to provide coverage of the small FOV 440, and simultaneously, or sequentially, detector emission array 434 may be operated in conjunction with detector array 438 to provide coverage of the small FOV 440, such that, in combination, they provide improved temporal resolution thereof.

Referring again to FIG. 7, according to another embodiment, source arrays 432, 434 may be positioned with respect to detector arrays 436, 438, such that improved temporal resolution of the small FOV 440 is obtained. Detector array 436 may be positioned to receive x-rays that pass through only small FOV 440 that emit from source array 432, and to receive x-rays that emit from source array 434 and pass through a peripheral region outside small FOV 440, but within large FOV 442. Likewise, detector array 438 may be positioned to receive x-rays that pass through only small FOV 440 that emit from source array 434, and to receive x-rays that emit from source array 432 and pass through a peripheral region outside small FOV 440, with in large FOV 442.

Additionally, one skilled in the art would recognize that the number of detector arrays and area source arrays is not limited to three detector arrays and area source arrays as illustrated in FIG. 7.

The embodiments described above in FIGS. 5-7 illustrate detector array and x-ray emission area sources that increase the temporal resolution of imaging in at least the cardiac, or small FOV region by providing redundant coverage thereof.

Accordingly, the x-ray emission area sources and detector arrays may operate simultaneously or in rapid succession to provide substantially increased angular coverage of the cardiac region during a reduced amount of gantry rotation, thereby improving the temporal resolution of the system. Furthermore, the detector arrays described herein may be circumferentially shorter than the area source arrays while still providing improved temporal resolution due to the increased coverage of the combined area sources and detector arrays. Also, in the above configurations, the area sources described herein may have focal spots that irradiate two or more detectors simultaneously, or focal spots may be dedicated for a given detector. Indeed, it is possible that one or more area sources each may be dedicated for a given detector array.

The embodiments described above also illustrate CT geometries having multiple emission points in the Z direction, thereby reducing conebeam artifacts. With the x-ray emission area sources extending in the Z direction, Z coordinate subject coverage equal or even greater than the Z length of the detector can be obtained. X-rays thereby impinge on the detectors with a reduced cone angle or axial divergence, thus reducing conebeam-related image artifacts. Additionally, the detector arrays described herein may be axially shorter than the area source arrays while still providing increased axial coverage without increasing conebeam-related image artifacts.

The embodiments described above also illustrate CT geometries which may operate with variable kVp operation. As an example, a first emission source, or plurality of emission sources, may be caused to operate at a first kVp, and a second emission source, or plurality of emission sources, may be caused to operate at a second kVp. Accordingly, images may be obtained wherein a first series of imaging data is acquired at the first kVp and a second series of imaging data is acquired at the second kVp. Additionally, detector arrays described herein may be operated in a simultaneous fashion to acquire x-rays passing through the object simultaneously. Alternatively, detector arrays described herein may be operated in an alternating fashion or sequentially to acquire data using x-rays which pass through the object over a short duration of time, and do not operate simultaneously.

Figure 8:
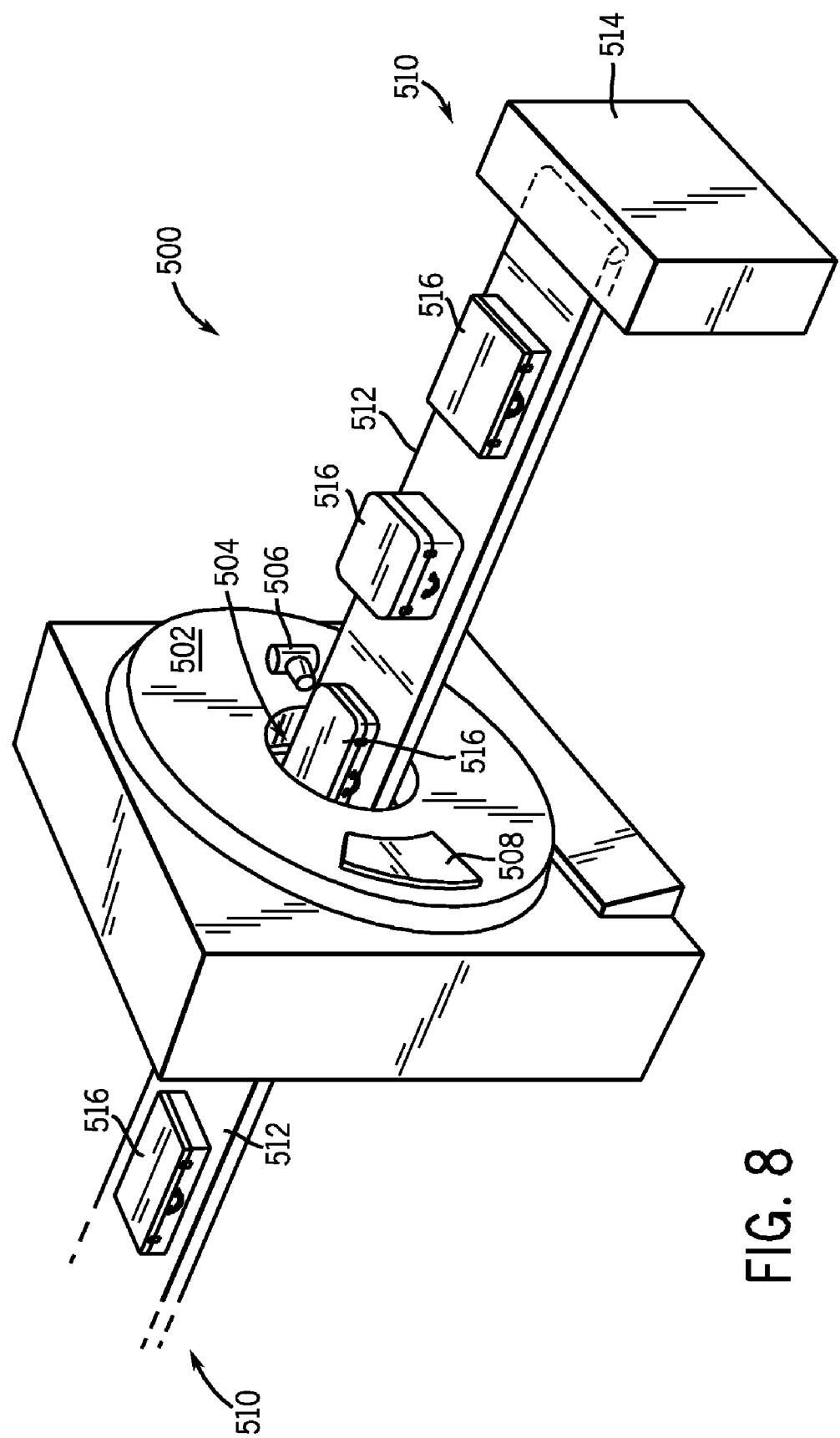
FIG. 8 is a pictorial view of a CT system for use with a non-invasive package inspection system incorporating an embodiment of the present invention.

Referring now to FIG. 8, package/baggage inspection system 500 includes a rotatable gantry 502 having an opening 504 therein through which packages or pieces of baggage may pass. The rotatable gantry 502 houses an embodiment of an x-ray emission area source 506 and detector array arrangement 508 described above in any of FIGS. 5-7. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

According to one embodiment of the present invention, a CT imaging system includes a rotatable gantry having an opening to receive an object to be scanned having a small field-of-view (FOV) inside a large FOV. A plurality of area sources is attached to the rotatable gantry, each area source includes a plurality of x-ray emission sources, wherein the plurality of area sources are configured to emit x-rays toward the object. A plurality of x-ray detector arrays is attached to the gantry and positioned such that at least a first detector array and a second detector array each receive x-rays that pass through at least the entire small FOV of the object.

According to another embodiment of the present invention, a method of fabricating a CT imaging system includes attaching a pair of multiple-emitter x-ray area sources to a rotatable gantry and attaching a plurality of detector arrays to the rotatable gantry. The method includes positioning a first detector array of the plurality of detector arrays such that x-rays emanating from a first x-ray area source of the pair of multiple-emitter x-ray area sources pass through an entire cardiac region of a subject are impinged thereon. The method further includes positioning a second detector array of the plurality of detector arrays such that x-rays emanating from a second x-ray area source of the pair of multiple-emitter x-ray area sources and passing through the entire cardiac region of a subject are impinged thereon.

According to yet another embodiment of the present invention, an imaging system includes a first area source having a plurality of point emission x-ray sources configured to emit x-rays toward a patient. The system includes a first detector array configured to receive x-rays emitted from the first area source that pass through at least a cardiac region of the patient, a second area source comprising a plurality of point emission x-ray sources configured to emit x-rays toward the patient, and a second detector array configured to receive x-rays emitted from the second area source that pass through at least the cardiac region of the patient.

The present invention has been described in terms of the preferred embodiment, and it is recognized that equivalents, alternatives, and modifications, aside from those expressly stated, are possible and within the scope of the appending claims.

What is claimed is:

1. A CT imaging system comprising:
 a rotatable gantry having an opening to receive an object to be scanned having a small field-of-view (FOV) inside a large FOV;
 a plurality of area sources attached to the rotatable gantry, each area source comprising a plurality of x-ray emission sources, wherein the plurality of area sources are configured to emit x-rays toward the object; and
 a plurality of x-ray detector arrays attached to the gantry and positioned such that at least a first detector array and a second detector array each receive x-rays that pass through at least the entire small FOV of the object.

2. The CT imaging system of claim 1 further comprising a line of symmetry passing transversely through a center of the rotatable gantry, and wherein the plurality of area sources and the plurality of detector arrays are positioned in a symmetric pattern about the line of symmetry.

3. The CT imaging system of claim 1 wherein at least one x-ray detector array of the plurality of x-ray detector arrays is positioned to receive x-rays from two area sources of the plurality of area sources.

4. The CT imaging system of claim 1 wherein at least one x-ray detector array of the plurality of x-ray detector arrays is positioned to receive x-rays from at least three area sources of the plurality of area sources.

5. The CT imaging system of claim 1 wherein each of the plurality of x-ray emission sources comprises one of a solid state x-ray source, a thermionic x-ray source, and a field emitter.

6. The CT imaging system of claim 1 wherein at least one of the plurality of x-ray detector arrays is positioned to receive x-rays that pass only through the large FOV of the object.

7. The CT imaging system of claim 1 wherein the small FOV comprises a cardiac region of the object.

8. The CT imaging system of claim 1 wherein at least one of the x-ray detector arrays is circumferentially narrower than at least one of the area sources.

9. The CT imaging system of claim 1 wherein at least one of the x-ray detectors is axially shorter than at least one of the area sources.

10. A method of fabricating a CT imaging system, the method comprising:
    attaching a pair of multiple-emitter x-ray area sources to a rotatable gantry;
    attaching a plurality of detector arrays to the rotatable gantry;
    positioning a first detector array of the plurality of detector arrays such that x-rays emanating from a first x-ray area source of the pair of multiple-emitter x-ray area sources and passing through an entire cardiac region of a subject are impinged thereon; and
    positioning a second detector array of the plurality of detector arrays such that x-rays emanating from a second x-ray area source of the pair of multiple-emitter x-ray area sources and passing through the entire cardiac region of a subject are impinged thereon.

11. The method of claim 10 further comprising symmetrically aligning the pair of multiple-emitter x-ray area sources with respect to a line of symmetry passing transversely through a center of the rotatable gantry.

12. The method of claim 10 further comprising attaching a plurality of emitters to a support structure to form a multiple-emitter x-ray area source, each of the plurality of emitters comprising one of a solid state x-ray source, a thermionic x-ray source, and a field emitter.

13. The method of claim 10 further comprising positioning a third detector array of the plurality of detector arrays such that x-rays emanating from each of the pair of multiple-emitter x-ray area sources and passing only through a non-cardiac region of the subject are impinged thereon.

14. The method of claim 10 further comprising:
    attaching a third multiple-emitter x-ray area source to the rotatable gantry;
    positioning a third detector array of the plurality of detector arrays such that x-rays emanating from the third x-ray area source and passing through the entire cardiac region of a subject are impinged thereon.

15. The method of claim 10 further comprising:
    positioning a third detector array of the plurality of detector arrays such that x-rays emanating from the first x-ray area source are impinged thereon, a first set of the x-rays passing through at least a portion of the cardiac region of the subject and a second set of the x-rays passing only through a portion of a non-cardiac region of the object.

16. An imaging system comprising:
    a first area source comprising a plurality of point emission x-ray sources configured to emit x-rays toward a patient;
    a first detector array configured to receive x-rays emitted from the first area source that pass through at least a cardiac region of the patient;
    a second area source comprising a plurality of point emission x-ray sources configured to emit x-rays toward the patient; and
    a second detector array configured to receive x-rays emitted from the second area source that pass through at least the cardiac region of the patient.

17. The imaging system of claim 16 further comprising a third detector array configured to receive x-rays emitted from both the first and second area sources that pass through at least a peripheral region of the patient.

18. The imaging system of claim 16 wherein the first detector array is further configured to receive x-rays emitted from the first area source that pass through the entire cardiac region of the patient, and wherein the second detector array is further configured to receive x-rays emitted from the second area source that pass through the entire cardiac region of the patient.

19. The imaging system of claim 16 wherein the first detector array is further configured to receive x-rays emitted from the first area source that pass only through a peripheral region of the patient, and wherein the second detector array is further configured to receive x-rays emitted from the second area source that pass only through a peripheral region of the patient.

20. The imaging system of claim 16 wherein the point emission sources of the first area source and second area source comprise one of a solid state x-ray source, a thermionic x-ray source, and a field emitter.

* * * * *